(12) United States Patent
Kane, Jr.

(10) Patent No.: US 9,454,765 B1
(45) Date of Patent: Sep. 27, 2016

(54) DETERMINING THE EFFECTS OF MODIFYING A NETWORK PAGE BASED UPON IMPLICIT BEHAVIORS

(75) Inventor: Francis J. Kane, Jr., Sammamish, WA (US)

(73) Assignee: IMDb.com, Inc., Seattle, WA (US)

( * ) Notice: Subject to any disclaimer, the term of this patent is extended or adjusted under 35 U.S.C. 154(b) by 1358 days.

(21) Appl. No.: 13/073,140

(22) Filed: Mar. 28, 2011

(51) Int. Cl.
*G06Q 30/02* (2012.01)
*G06F 19/24* (2011.01)

(52) U.S. Cl.
CPC .............. *G06Q 30/02* (2013.01); *G06F 19/24* (2013.01); *G06Q 30/0269* (2013.01)

(58) Field of Classification Search
CPC .............. G06Q 30/02; G06Q 30/0269; G06F 11/3688; G06F 19/24
See application file for complete search history.

(56) References Cited

U.S. PATENT DOCUMENTS

| | | | | |
|---|---|---|---|---|
| 6,160,536 A * | 12/2000 | Forest | ...................... | G06F 3/018 345/157 |
| 6,562,077 B2 * | 5/2003 | Bobrow | ............ | G06F 17/30011 382/306 |
| 6,665,841 B1 * | 12/2003 | Mahoney | ........... | G06K 9/00463 707/E17.023 |
| 7,363,282 B2 * | 4/2008 | Karnawat et al. | ............... | 706/45 |
| 7,870,491 B1 * | 1/2011 | Henderson | ............ | G06F 9/4446 715/745 |
| 8,024,660 B1 * | 9/2011 | Quinn | ................... | G06F 9/4446 715/745 |
| 8,487,959 B1 * | 7/2013 | Khan | ....................... | G06F 3/013 345/619 |
| 8,704,792 B1 * | 4/2014 | Kataoka | ................ | G06F 3/0416 345/173 |
| 8,868,565 B1 * | 10/2014 | Zhong | ............... | G06F 17/30707 707/740 |
| 8,997,081 B1 * | 3/2015 | Manion | ...................... | G06F 8/65 717/168 |
| 2006/0123340 A1 * | 6/2006 | Bailey | ................. | G06F 9/44526 715/700 |
| 2008/0163065 A1 * | 7/2008 | Vartiainen et al. | ............ | 715/738 |
| 2008/0228910 A1 * | 9/2008 | Petri | ................. | G06F 17/30905 709/224 |
| 2010/0131835 A1 * | 5/2010 | Kumar et al. | ................. | 715/205 |
| 2010/0169792 A1 * | 7/2010 | Ascar et al. | ................... | 715/744 |
| 2010/0198768 A1 * | 8/2010 | Zhou et al. | ....................... | 706/47 |
| 2011/0137737 A1 * | 6/2011 | Baird | ................. | G06Q 30/0272 705/14.73 |
| 2011/0206283 A1 * | 8/2011 | Quarfordt | ............ | G06K 9/0061 382/220 |
| 2011/0252356 A1 * | 10/2011 | Morris | ................... | G06F 9/4443 715/772 |
| 2012/0023457 A1 * | 1/2012 | Lai et al. | ........................ | 715/863 |
| 2012/0036468 A1 * | 2/2012 | Colley | ................ | G06F 3/04886 715/773 |
| 2012/0140255 A1 * | 6/2012 | Tanaka | ..................... | G06F 9/445 358/1.13 |
| 2012/0146891 A1 * | 6/2012 | Kalinli | .................... | H04N 19/33 345/156 |
| 2012/0151329 A1 * | 6/2012 | Cordasco | ....................... | 715/234 |
| 2013/0227392 A1 * | 8/2013 | Zhong | ................ | G06F 17/3089 715/234 |

* cited by examiner

*Primary Examiner* — Ryan Pitaro
(74) *Attorney, Agent, or Firm* — Thomas | Horstemeyer, LLP

(57) ABSTRACT

Disclosed are various embodiments for determining the effects of modifying a network page based at least upon the implicit behaviors of users. An executable network page is generated to record the implicit behaviors of users. A position density map is then generated from the recorded implicit behavior to identify the content on the network page that has a high or low level of user interaction. The position density map is then analyzed to determine if the content on the network page needs to be revised. Subsequent A/B tests relating to revisions made to the network page may be run to ascertain the effect of changing the network page using the position density map.

20 Claims, 9 Drawing Sheets

DETERMINING THE EFFECTS OF MODIFYING A NETWORK PAGE BASED UPON IMPLICIT BEHAVIORS

BACKGROUND

Users of a content delivery system often interact with a user interface delivered by a system via a network on a client. There are mechanisms that are designed to elicit feedback from the user, such as, for example, winks, nudges, pings, thumbs up/down, hot or not ratings, as well as surveys or questionnaires. However, these mechanisms require explicit actions on behalf of the user. Furthermore, many users choose not to participate in such feedback mechanisms even when it is as simple as selecting a thumbs up button or checking a button to indicate the content was helpful.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the disclosure. Moreover, in the drawings, like reference numerals designate corresponding parts throughout the several views.

DETAILED DESCRIPTION

The present disclosure relates to determining the effects of modifying a network page based upon the implicit behaviors of a user. Typically, to measure how users respond to content of a network page, traditional 'weblabs' or NB tests work by presenting two or more different sets of content to users and measuring how the users respond. However, such arrangements may overlook other indicators identifying content of the network page that have captured the attention of the user even if the user does not make an explicit action.

Various embodiments of the present disclosure relate to generating a network page that records implicit behaviors of users interacting with the network page. A position density map is then generated from the recorded implicit behavior to identify the content on the network page that has a high or low level of user interaction. The position density map is then analyzed to determine if the content on the network page needs to be revised. Subsequently, NB tests relating to revisions made to the network page may be run to ascertain the effect of changing the network page using the position density map. In the following discussion, a general description of the system and its components is provided, followed by a discussion of the operation of the same.

Figure 1:
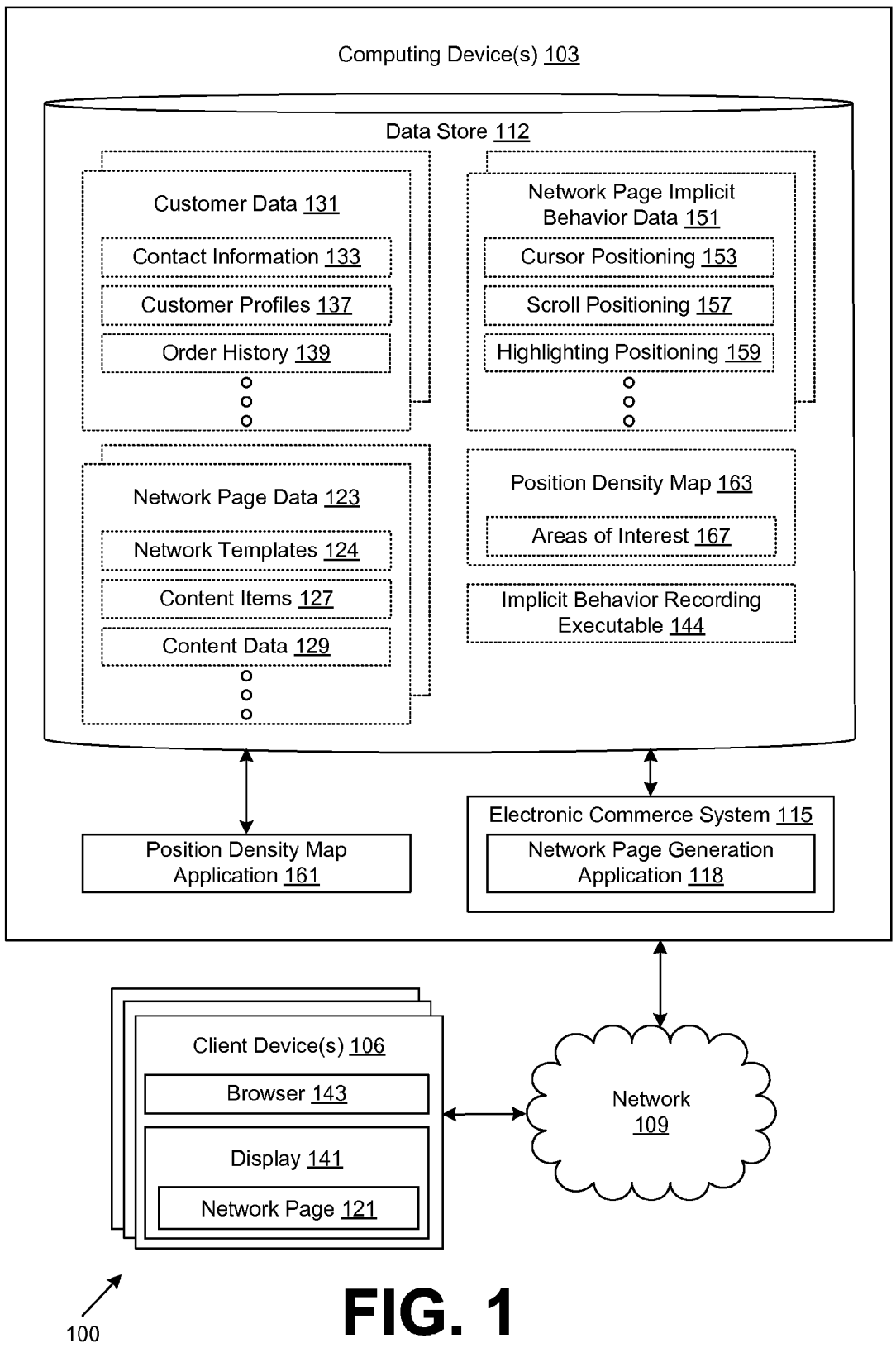
FIG. 1 is a drawing of networked environment according to various embodiments of the present disclosure.

With reference to FIG. 1, shown is a networked environment 100 according to various embodiments. The networked environment 100 includes one or more computing devices 103, and one or more client devices 106 coupled to a network 109. The network 109 includes, for example, the Internet, intranets, extranets, wide area networks (WANs), local area networks (LANs), wired networks, wireless networks, or other suitable networks, etc., or any combination of two or more such networks.

The computing device 103 may comprise, for example, a server computer or any other system providing computing capability. Alternatively, a plurality of computing devices 103 may be employed that are arranged, for example, in one or more server banks or computer banks or other arrangements. For example, a plurality of computing devices 103 together may comprise a cloud computing resource, a grid computing resource, and/or any other distributed computing arrangement. Such computing devices 103 may be located in a single installation or may be distributed among many different geographical locations. For purposes of convenience, the computing device 103 is referred to herein in the singular. Even though the computing device 103 is referred to in the singular, it is understood that a plurality of computing devices 103 may be employed in the various arrangements as described above.

Various applications and/or other functionality may be executed in the computing device 103 according to various embodiments. Also, various data is stored in a data store 112. The data store 112 is accessible to the computing device 103 and may be representative of a plurality of data stores 112 as can be appreciated. The data stored in the data store 112 for example, is associated with the operation of the various applications and/or functional entities described below.

The data stored in the data store 112 may comprise network page data 123, customer data 131, an implicit behavior recording executable 144, network page implicit behavior data 151, a position density map 163, revised network pages, and potentially other data. The network page implicit behavior data 151 may comprise data relating to the implicit behaviors of a user within a network page including cursor positioning 153, scroll positioning 157, and highlighting positioning 159. The network page implicit behavior data 151 may further comprise the time the user spends hovering the cursor at a position within the network page, highlighting text at a position within the network page, maintaining a scroll bar in a given position in the network page, and other implicit behaviors. The customer data 131 may comprise data relating to the user that requests the network page and may include contact information 133, customer profiles 137, order history 139, and other customer data. The implicit behavior recording executable 144 records the network page implicit behavior data 151. Lastly, the position density map 163 identifies positions within the network page having a high level of user interaction based at least upon the network page implicit behavior data 151. In addition, other information may be gleaned from the position density map 163, such as, for example, whether positions with a high level of user interaction are located at the top, center and/or bottom of the network page The components executed on the computing device 103, for example include, an electronic commerce system 115 that includes a network page generation application 118, and a position density map application 161, as well as other applications, services, processes, systems, engines, or functionality not discussed in detail herein. To this end, the electronic commerce system 115 acts as a gateway through which requests are received and responses transmitted as can be appreciated. The network page generation application 118 generates network pages embedded with the implicit behavior recording executable 144, such as, for example, web pages, mobile application screens, or other content. The position density map application 161 generates the position density map 163 from at least the network page implicit behavior data 151. It is understood that other applications and components, such as an application implementing the hypertext transport protocol, may be executed on the computing device 103 beyond those described herein.

The electronic commerce system 115 implemented in the computing device 103 may, in some embodiments, facilitate the online viewing and/or purchasing of items and products, or other services that involve delivering content over a network 109. Although the present disclosure is described in conjunction with the operation of an electronic commerce system 115, it is understood that the functionality described may apply to many other contexts. For example, the functionality described herein may be employed to improve interaction by users with respect to any network site.

The principles described herein may apply to a network site that simply relays content in terms of images, text, video, or other content to be viewed by users. To this end, the principles described herein may help to make the presentation of such content more effective or user friendly, etc.

As another example, it may be the case that a network site serves up network pages having forms and content that are presented to users, where the user fills out the forms for some purpose. For example, such sites could be government sites that provide information and forms to be filled by citizens. The principles described herein may be employed to improve network pages that include such forms and information in an effort to obtain more accurate and complete information from citizens, and to relay information in a more effective manner.

Additionally, the computing device 103 may execute applications such as the network page generation application 118. The network page generation application 118 may access the network page data 123, such as the network templates 124 to specify the placement of user interface elements in the network page and/or the content data 129 to determine the types of content in the network page (e.g. advertising content, service-based content, informational content, entertainment content, etc.). Additionally, the network page generation application 118 may access the content 127 to specify information associated with each item such as, but is not limited to, taxonomies, descriptions, product details, metadata, keywords, and/or other classification data/information. It is understood that the content 127 of the network page 121 may comprise text, images, widgets, sounds, colors, graphics, videos, executable code, or other content elements.

As a non-limiting example, the network page generation application 118 may use the network templates 124 that specify the placement of text, images, buttons, etc., which can include user interface elements that facilitate the purchase of an item (e.g., an "Add to Cart" button). The network page generation application 118 may also embed the network page with the implicit behavior recording executable 144 to record the implicit behaviors of the user for whom the network page is rendered. Such implicit behaviors may comprise locations at which the user positions a cursor within the network page or other implicit behaviors as will be described.

When deemed appropriate, the position density map application 161 may be executed to generate the position density map 163 by plotting the cursor positionings 153, the scroll positionings 157, the highlighting positionings 159 and other implicit behavior data associated with the network page. The position density map application 161 then identifies areas of interest 167 on the position density map 163 that have a number of plotted points per unit area above or below a predefined threshold, thereby indicating a high or low level of user interaction. The position density map application 161 then may correlate the areas of interest 167 to the content of the network page. In one embodiment, analysis of the position density map 163 and the areas of interest 167 may indicate changes that should be incorporated into the network page. Subsequent A/B testing may then be run to ascertain the effect of the changes made to the network page relative to the original version of the network page.

As a non-limiting example, if a user repeatedly places the cursor in a particular location within a network page, then the implicit behavior recording executable 144 will repeatedly record the position of the cursor at this location at predefined intervals. The position density map application 161 then generates a position density map 163 based on the recorded locations. The position density map application 161 then identifies areas of interest 167 based on the areas or spots with an increased number of plotted positions. In this example, the region where the user repeatedly places the cursor is an area of interest 167 having a high level of user interaction. The position density map application 161 then correlates the areas of interest 167 to the content of the network page. The network page may then be revised by moving the content that correlates to the areas of interest 163 to a location with a higher level of user visibility. Subsequent A/B testing may then be run to ascertain the effect of changing the network page.

In another non-limiting example, the position density map application 161 may qualify areas of interest 163 based on various factors, including the type of content, the position of the content within the network page, the distance between the content and the network page fold, as well as any other relevant factors.

In a non-limiting example, the pre-defined threshold values are based on the type of content. If the network page 121 comprises, for example, a first region that includes entertainment content and a second region that includes advertising content and the objective is to generate profits from advertisements, then the region of the advertising content may be assigned a low threshold value of plotted points per unit area to more easily identify areas of interest, whereas the region with the entertainment content may be assigned a relatively high threshold value.

In another non-limiting example, the pre-defined thresholds values are based on the position of the content within the network page 121. If one objective is to generate profits and content positioned in the middle of the network page 121 is associated with high profitability, then the content in the middle of the network page 121 may have a lower pre-defined threshold value of plotted points per unit area. In this example, the content positioned at the top and bottom of the network page 121 may be associated with higher pre-defined threshold values.

In yet another non-limiting example, the pre-defined thresholds values are based on the distance between the content and the network page fold. For instance, if users have a tendency to only view content above the network page fold, then content above the network page fold may be assigned a lower pre-defined threshold than content positioned below the network page fold.

Subsequently, the position density map application 161 may then generate an additional network page 121 by rearranging the content of the network page 121. In one embodiment, content 127 may be moved into positions relative to the pre-defined threshold values as described above. Regardless of the changes made, the position density map application 161 may then store the additional network page 121 on the computing device 103.

The client device 106 may be representative of a plurality of client devices 106 that may be coupled to the network 109. The client devices 106 may comprise, for example, a processor-based system, such as a computer system. Such a computer system may be embodied in the form of a desktop computer, a laptop computer, a personal digital assistant, an electronic book reader, a mobile device (e.g. cellular telephone, smart phone, etc.), set-top box, music players, web pads, tablet computer systems, or other devices with like capability. The client device 106 includes a display 141 upon which the network page 121 is rendered.

The client device 106 may be configured to execute various applications, such as a browser 143 and/or other applications. The browser 143 may be executed in the client device 106, for example, to access the network page 121, such as web pages, and the associated content served up by the computing device 103 and/or other servers. The client device 106 may be configured to execute applications beyond the browser 143 such as, for example, email applications, instant message applications, and/or other applications. It is understood that the network page 121 may include any presentation or delivery of information that may be accessed through the browser 143 in the client device 106.

Next, a general description of the operation of the various components of the networked environment 100 is provided. To begin, the browser 143 of the client device 106 sends a request for the network page 121 to the electronic commerce system 115 of the computing device 103. Next, the network page generation application 118 generates the network page 121 by accessing the network page data 123 and the implicit behavior recording executable 144. The electronic commerce system 115 then sends the requested network page 121 to the browser 143 on the client device 106. The implicit behavior recording executable 144 then records the implicit behaviors of the user while the user interacts with the network page 121 rendered by the browser 143.

At discrete points of time, the implicit behavior recording executable 144 records the interactions between the user and the network page 121, including where the user hovers or moves a cursor, where the user positions or moves one or more scroll bars, and/or where the user highlights content associated with the network page 121. Also, the interactions may include the time the user spends hovering a cursor, highlighting certain positions within the network page 121, or holding a scroll bar at a given position, and/or other implicit behaviors. Thus, the implicit behaviors of the user may be recorded in terms of a log of positions of a cursor or scroll bar over a period of time. The implicit behavior may also be recorded in terms of a log of text that was highlighted at certain times, or in other terms. The implicit behavior recording executable 144 then transmits the network page implicit behavior data 151 from the client device 106 to the electronic commerce system 115 on the computing device 103 through network 109 to store as the network page implicit behavior data 151 within the data store 112.

Next, the position density map application 161 creates the position density map 163 by plotting points associated with a particular implicit behavior stored within the network page implicit behavior data 151. That is, the position density map application 161 may generate the position density map 163 with plotted points from, for example, the cursor positioning 153. Alternatively, the position density map application 161 may generate the position density map 163 by plotting points associated with multiple implicit behaviors recorded in the network page implicit behavior data 151, including the cursor positioning 153, the scroll positioning 157, the highlighting positioning 159, and any other relevant data. Accordingly, the position density map application 161 may generate the position density map 163 associated with a particular implicit behavior or may generate the position density map 163 associated with two or more recorded implicit behaviors.

The position density map application 161 then identifies locations with a high number of plotted points on the position density map 163, as well as other appropriate data, such as explicit behavior data, to identify areas of interest 167. The position density map application 161 then correlates the areas of interest 167 to the content of the network page 121, thereby identifying the content of the network page 121 associated with a high level of user interaction.

Additionally, the position density map application 161 may then implement an action to generate an additional network page 121 based on the identified areas of interest 167, the content of the network page 121, position density values from the position density map 163, or other relevant data. In one non-limiting example, the position density map application 161 may implement the action of moving the content having a high level of user interaction to positions with high visibility. Subsequently A/B testing relating to the changes made to the network page 121 may be run to ascertain the effects of revising the network page 121 using the implicit behavior data. For example, the results of the NB testing may comprise comparative profit data associated with rendering the additional network page 121 and the original network page 121. The results of the NB testing may determine whether changes have provided various sought after benefits or results, including click throughs, ratings provided, surveys filled out, purchases made, requests made for information, objective page activity, and other relevant results.

For example, click throughs involve users clicking various links to access additional network content as desired. Ratings involve users indicating whether identified content was desirable or useful. Surveys filled out is a result in which users take the time to fill out surveys for various purposes or submit comments, etc. Purchasing data may indicate if an increase in profits were generated from the additional network page 121. Requests for additional data may indicate if the user requested information from the additional network page 121. Lastly, objective page data may involve whether the user interacts more or less with an objective page associated with the additional network page 121, wherein the objective page is a page with important information. It is understood that the aforementioned types of results or benefits of A/B testing are merely examples of the many results that may be obtained from A/B testing.

In one embodiment of the present disclosure, the areas of interest 167 on the position density map 163 may be established only after a threshold density or a point per unit area has been reached. In other words, the area of interest 167 on the position density map 163 is established only after a threshold number of points are plotted in a certain area on the position density map 163. Other examples of establishing predefined thresholds should be appreciated.

In another embodiment of the present disclosure, the implicit behavior recording executable 144 records the network page implicit behavior data 151 on a periodic basis within a user's session. The user session may start, for example, when the user first moves the cursor within the network page 121 and ends when the user navigates away or exits from the network page 121. Accordingly, the network page implicit behavior data 151 may log data at pre-defined time periods within the user session, such as every second, tenths of a second, or other time intervals.

Additionally, in one embodiment of the present disclosure, the position density map application 161 may establish areas of interest 167 based on other relevant factors, including explicit data of the user associated with the network page 121 or data indicating the cursor of the user is positioned outside of the network page 121. That is, if the user has a tendency to idle the cursor outside the network page 121, then JavaScript code or other code embedded within the network page 121 may stop logging positions when the cursor exits from within the network page 121.

In an alternate embodiment, multiple versions of a network page 121 may be generated, wherein each of the network pages 121 comprises different content layout and/or data. The implicit behaviors of a user may then be recorded for each version of the network page 121 viewed by the user. The position density map application 161 may then generate the position density map 163 for each version of the network page 121 from the implicit behaviors of the users. NB testing may then analyze the position density maps 163 associated with each version of the network page 121 to compare and contrast the implicit behaviors of users for each of the trial network pages 121 and/or identify the content in each of the trial network pages 121 that effectively captures the interest of the users. Thus, NB testing may be used to compare and contrast multiple sets of implicit behaviors associated with multiple network pages having different content layouts to determine which version provides the best results in accordance with a goal or objective of the network page. That is, the goal or objective may comprise increasing profitability by increasing the number of items purchased by the users. Further, the goal or objective may comprise achieving high user ratings, increasing user participation in surveys, increasing user navigation through clicking on links within the network page, or other goal or objective.

Figure 2:
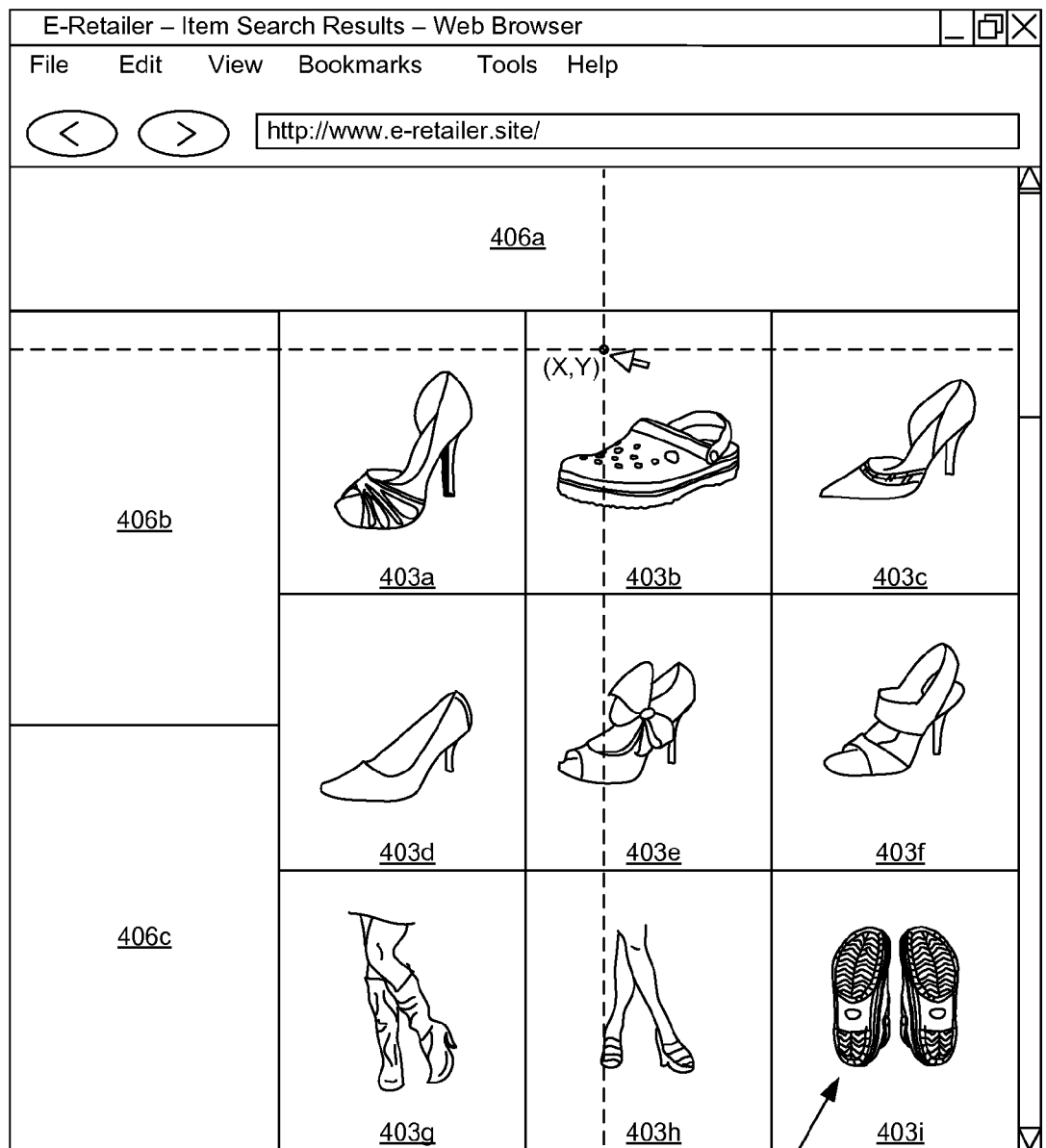
FIGS. 2-4 are drawings of examples of a network page generated in the networked environment of FIG. 1 according to various embodiment of the present disclosure.

Turning now to FIG. 2, shown is one example which depicts a network page 121a embedded with an implicit behavior recording executable 144 (FIG. 1) within a display 141 (FIG. 1) of a client device 106 (FIG. 1). The network page generation application 118 (FIG. 1) may divide the network page 121a into content placement blocks 403a-i, top navigation slot 406a, left navigation slot 406b and bottom left slot 406c. Each of the content blocks 403 may contain content associated with the network page 121a for the user to view. The implicit behavior recording executable 144 (FIG. 1) locates where a user positions a cursor within the network page 121a by identifying an "x" and "y" coordinate relative to the entire display 141. In the depicted example, the implicit behavior recording executable 144 has identified the coordinates x and y as a cursor positioning 153 (FIG. 1).

Figure 3:
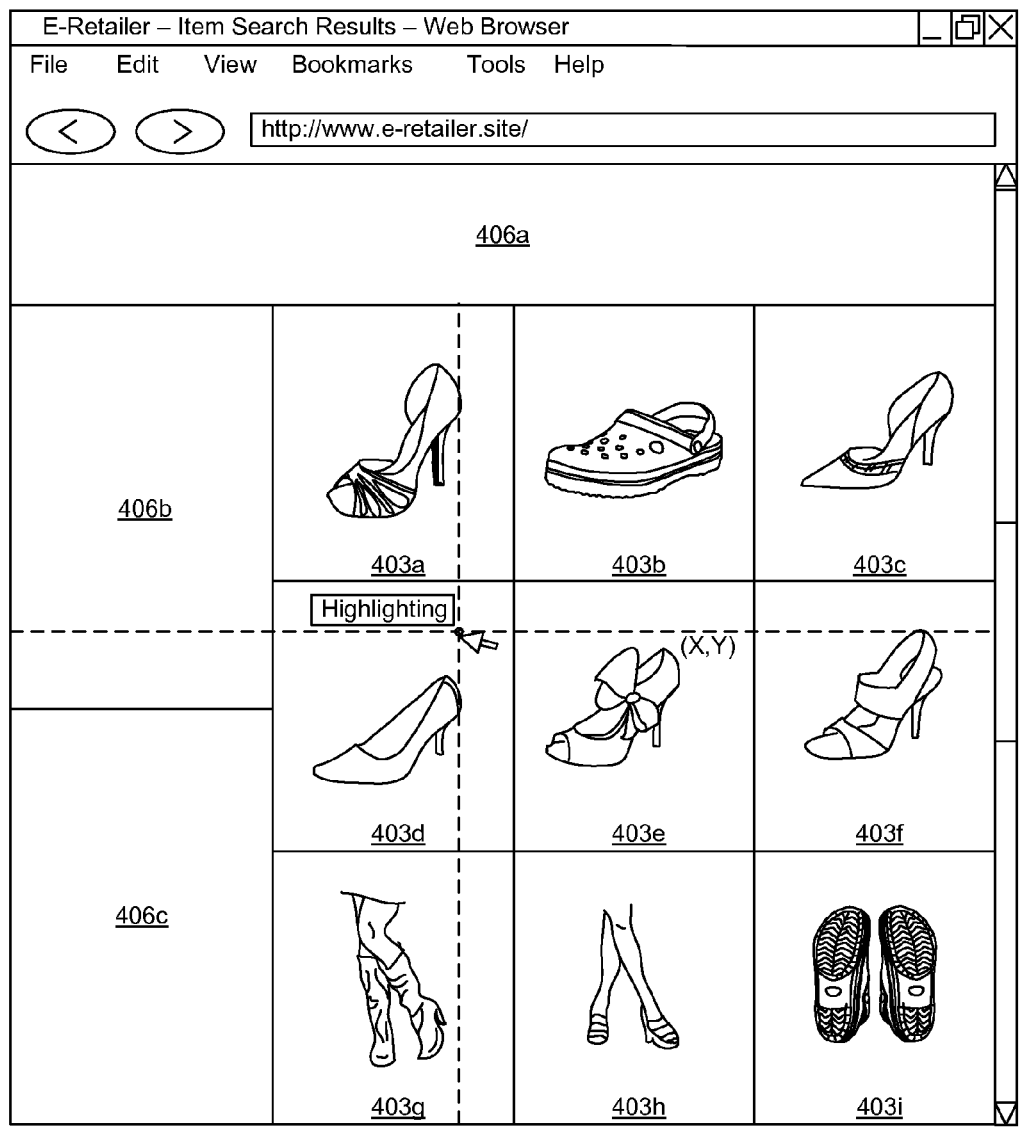

Turning now to FIG. 3, shown is one example which depicts a network page 121b embedded with an implicit behavior recording executable 144 (FIG. 1) within a display 141 (FIG. 1) of a client device 106 (FIG. 1). The network page generation application 118 (FIG. 1) may divide the network page 121b into content placement blocks 403a-i, top navigation slot 406a, left navigation slot 406b and bottom left slot 406c. Each of the content blocks 403 may contain content associated with the network page 121b for the user to view. The network page generation application 118 locates where a user highlights text within the network page 121b by identifying an x and y coordinate relative to the entire display 141. In the depicted example, the implicit behavior recording executable 144 has identified the coordinates x and y as a highlighting positioning 159 (FIG. 1) and/or may record the text highlighted.

Figure 4:
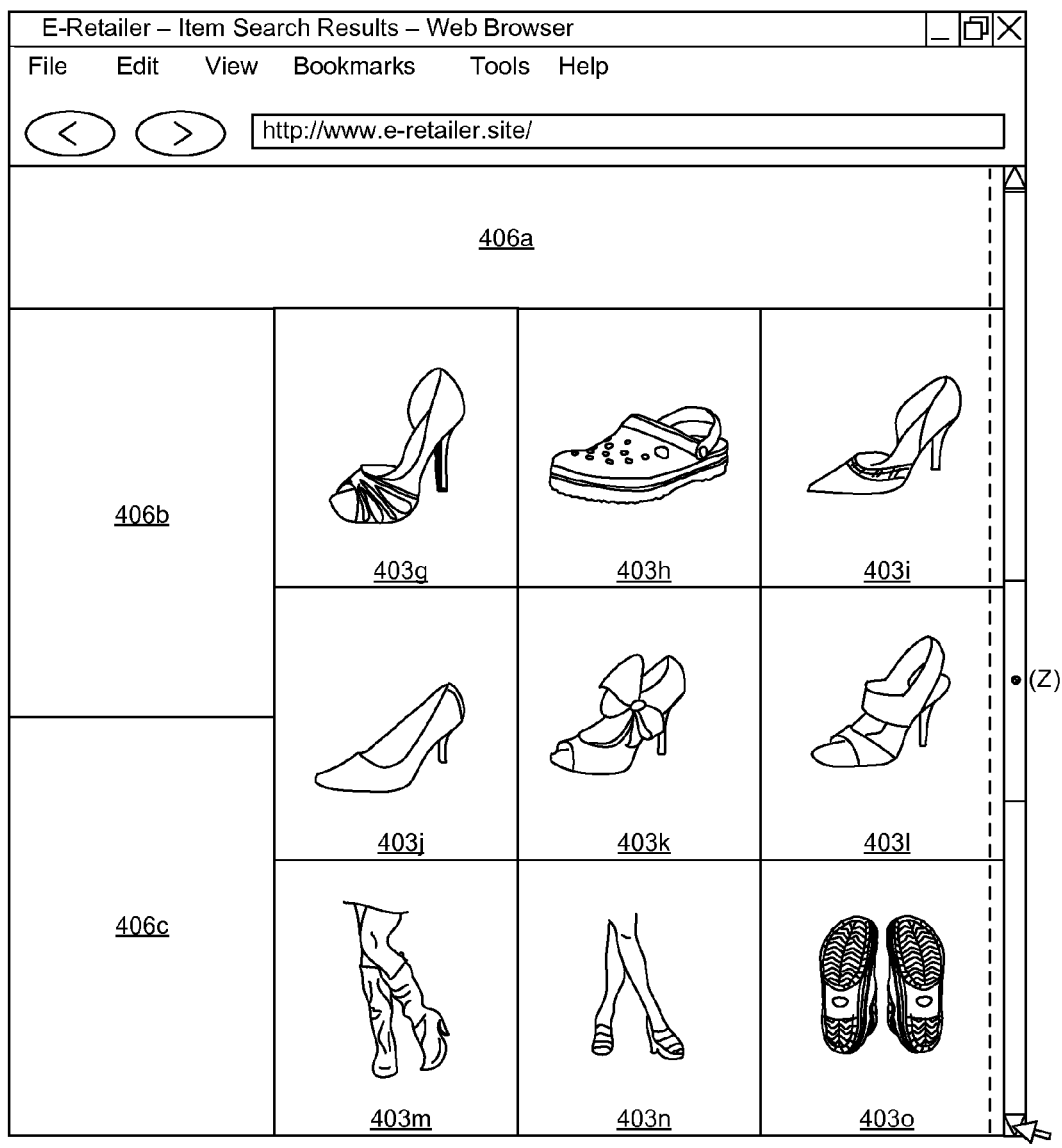

Turning now to FIG. 4, shown is one example which depicts a network page 121c embedded with an implicit behavior recording executable 144 (FIG. 1) within a display 141 (FIG. 1) of a client device 106 (FIG. 1). The network page generation application 118 (FIG. 1) may divide the network page 121c into content placement blocks 403g-o, top navigation slot 406a, left navigation slot 406b and bottom left slot 406c. Each of the content blocks 403 may contain content associated with the network page 121c for the user to view. The network page generation application 118 locates where a user has moved at least one scroll bar within the network page 121c by identifying a "z" coordinate relative to the entire display 141 (FIG. 1). In the depicted example, the implicit behavior recording executable 144 (FIG. 1) has identified the coordinate z as a scroll positioning 157 (FIG. 1).

Figure 5:
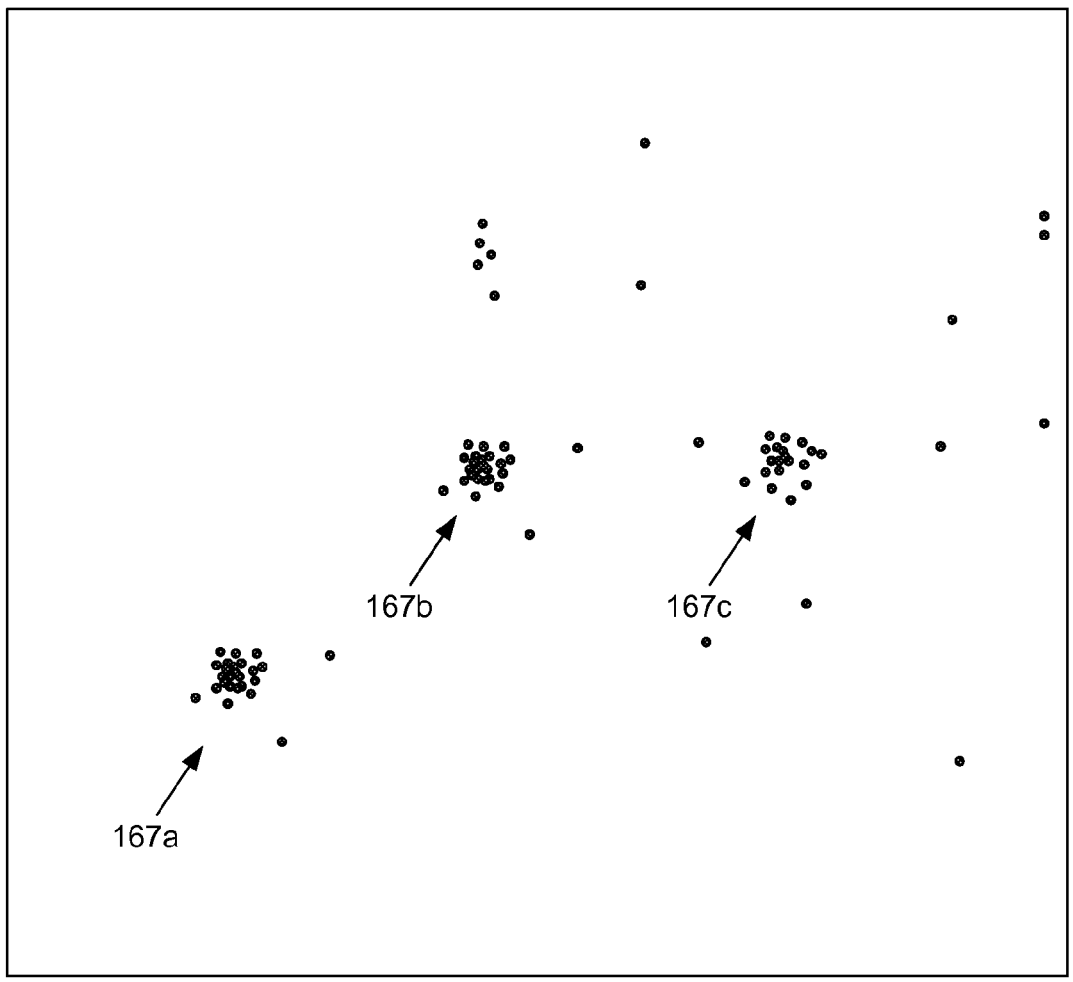
FIG. 5 is a drawing of an example of a position density map with areas of interest generated in the networked environment of FIG. 1 according to various embodiment of the present disclosure.

Turning now to FIG. 5, shown is one example which depicts a position density map 163 generated by the position density map application 161 (FIG. 1). The position density map application 161 plots cursor positionings 153 (FIG. 1), scroll positionings 157 (FIG. 1), highlighting positionings 159 (FIG. 1), and other implicit behavior data. The position density map application 161 may identify areas of interest 167 if there are a high number of plotted positions within a certain region of the network page 121 (FIG. 1). In the depicted example, the position density map application 161 has identified areas of interest 167a, 167b and 167c on the position density map 163.

Figure 6:
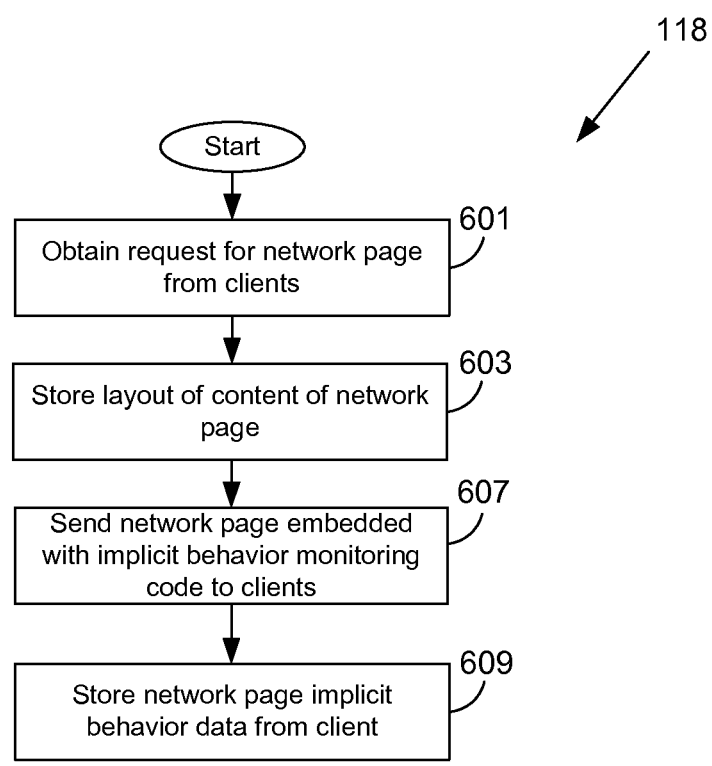
FIG. 6 is a flowchart illustrating an example of the functionality of a network page generation application implemented in a computing device in networked environment of FIG. 1 according to an embodiment of the present disclosure.

Turning now to FIG. 6, shown is a flowchart that provides one example of the operation of a portion of the network page generation application 118 (FIG. 1) according to various embodiments. It is understood that the flowchart of FIG. 6 provides merely an example of the many different types of functional arrangements that may be employed to implement the operation of the portion of the network page generation application 118 as described herein. As an alternative, the flowchart of FIG. 6 may be viewed as depicting an example of steps of a method implemented in the computing device 103 (FIG. 1) according to one or more embodiments.

Beginning with box 601, the electronic commerce application 115 (FIG. 1) receives a request for a network page 121

(FIG. 1) from a client device 106 (FIG. 1). Next, in box 603, the network page generation application 118 generates the network page 121 requested by the client device 106 and stores network page data 123 (FIG. 1) associated with the requested network page 121 in data store 112 (FIG. 1). Embedded within the network page 121 is the implicit behavior recording executable 144 (FIG. 1).

In box 607, the electronic commerce system 115 sends the network page 121 embedded with the implicit behavior recording executable 144 to the client device 106. Next, in box 609, the electronic commerce system 115 receives the implicit behavior data 151 (FIG. 1) from the client device 106 to store in the data store 112, where the implicit behavior data 151 is generated by the implicit behavior recording executable 144.

Figure 7:
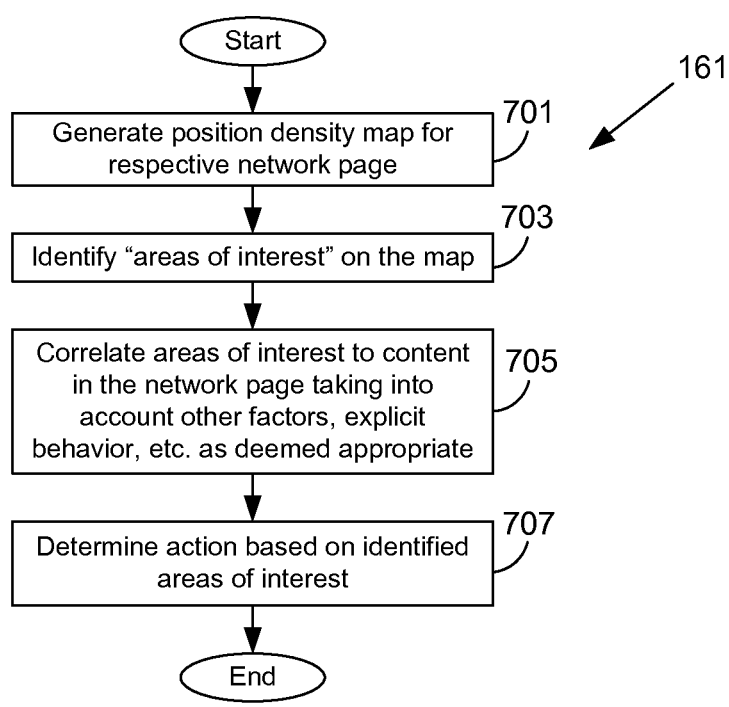
FIG. 7 is a flowchart illustrating an example of functionality of a position density map application implemented in a computing device in networked environment of FIG. 1 according to an embodiment of the present disclosure.

Referring next to FIG. 7, shown is a flowchart that provides one example of the operation of a portion of the position density map application 161 (FIG. 1) according to various embodiments. It is understood that the flowchart of FIG. 7 provides merely an example of the many different types of functional arrangements that may be employed to implement the operation of the portion of the position density map application 161 as described herein. As an alternative, the flowchart of FIG. 7 may be viewed as depicting an example of steps of a method implemented in the computing device 103 (FIG. 1) according to one or more embodiments.

Beginning with box 701, the position density map application 161 plots the coordinates associated with cursor positionings 153 (FIG. 1), scroll positionings 157 (FIG. 1), highlighting positionings 159 (FIG. 1), and any other relevant data to generate the position density map 163 (FIG. 1) associated with the network page 121 (FIG. 1). The position density map application 161 may plot network page implicit behavior data 151 from multiple users viewing instances of the network page 121. Next, in box 703, the position density map application 118 analyzes the plotted coordinates on the position density map 163 to identify the areas of interest 167 (FIG. 1). In particular, if a particular region of the position density map 163 contains a high number of plotted coordinates, then the position density map application 161 may identify that region as an area of interest 167.

In box 705, the position density map application 161 correlates the areas of interest 167 on the position density map 163 to content of the network page 121 by examining the position of the content in the network page 121 as is indicated in the stored network page data 123 (FIG. 1) that correspond to areas of interest 167. Also, the position density map application 161 may take into account other data, such as the user's explicit behavior, the nature of the content as described above, and/or other data if deemed appropriate. For example, if a user purchases a particular item, then the position density map application 161 may also plot coordinates on the position density map 163 to identify the locations of the explicit behaviors of the user. Lastly, in box 707, the position density map application 161 determines an action to take with respect to the network page 121 based on the areas of interest 167. Examples of action to be taken are discussed below.

Figure 8:
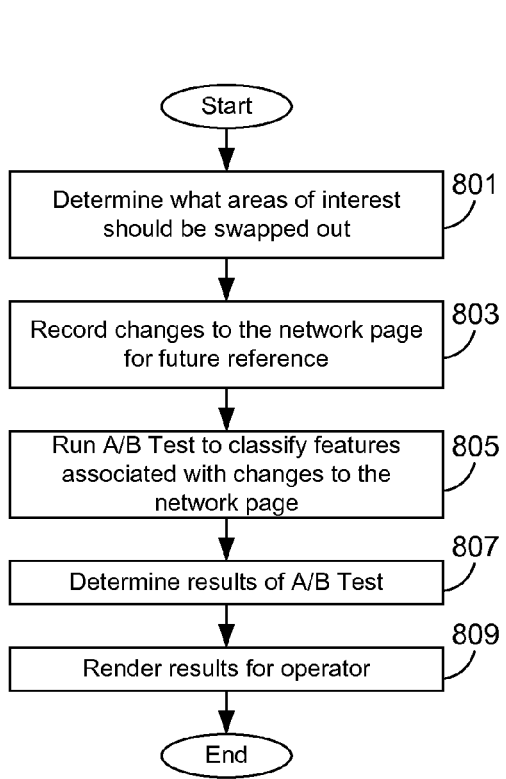
FIG. 8 is a flowchart illustrating an example of functionality of a position density map application implemented in a computing device in the networked environment of FIG. 1 according to various embodiments of the present disclosure.

Referring next to FIG. 8, shown is a flowchart that provides one example of the operation of a portion of the position density map application 161 (FIG. 1) according to various embodiments. It is understood that the flowchart of FIG. 8 provides merely an example of the many different types of functional arrangements that may be employed to implement the operation of the portion of the position density map application 161 as described herein. As an alternative, the flowchart of FIG. 8 may be viewed as depicting an example of steps of a method implemented in the computing device 103 (FIG. 1) according to one or more embodiments.

Beginning in box 801, the position density map application 161 may determine that certain areas of interest 167 (FIG. 1) should be swapped with each other, thereby creating a revised network page 121 (FIG. 1). For example, the content of the network page 121 associated with the areas of interest 167 having a low level of user interaction may be moved to the bottom of the network page and the content of the network page 121 associated with the areas of interest 167 with a high level of user interaction may be moved to the top of the network page. In box 803, the position density map application 161 stores the changes to the network page 121 in the data store 112 (FIG. 1). In box 805, A/B testing identifies the effect of changing the network page 121. For example, A/B testing may compare the number of purchases that are associated with rendered instances of the original network page and relate to the number of purchases that are associated with rendered instances of the revised network page. In other words, the NB testing can evaluate if a revised network page 121, based on implicit data, is more profitable than the original network page 121. In box 807, the position density map application 161 generates results from the NB testing. In box 809, the position density map application 161 stores the results of the NB test.

Figure 9:
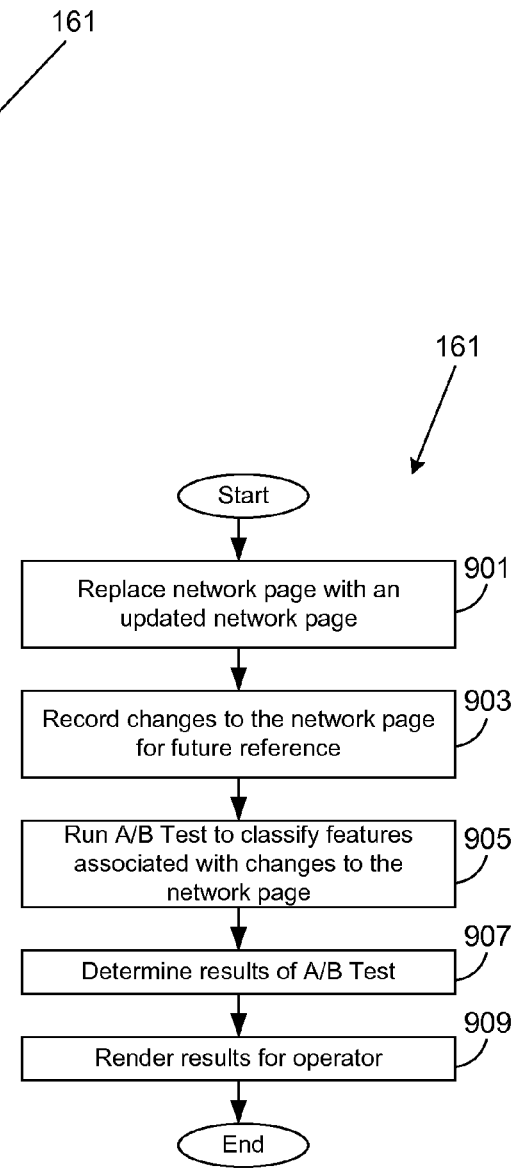
FIG. 9 is a flowchart illustrating an example of functionality of a position density map application implemented in a computing device in the networked environment of FIG. 1 according to various embodiments of the present disclosure.

Referring next to FIG. 9, shown is a flowchart that provides one example of the operation of a portion of the position density map application 161 (FIG. 1) according to various embodiments. It is understood that the flowchart of FIG. 9 provides merely an example of the many different types of functional arrangements that may be employed to implement the operation of the portion of the position density map application 161 as described herein. As an alternative, the flowchart of FIG. 9 may be viewed as depicting an example of steps of a method implemented in the computing device 103 (FIG. 1) according to one or more embodiments.

Beginning in box 901, the position density map application 161 replaces the network page 121 (FIG. 1) with an additional network page 121. In box 903, the position density map application 161 stores the changes to the network page 121 in the data store 112 (FIG. 1). In box 905, A/B testing identifies the effect of changing the network page 121. In box 907, the position density map application 161 evaluates the NB testing to determine the results of the A/B test. In box 909, the position density map application 161 stores the results of the NB test.

Figure 10:
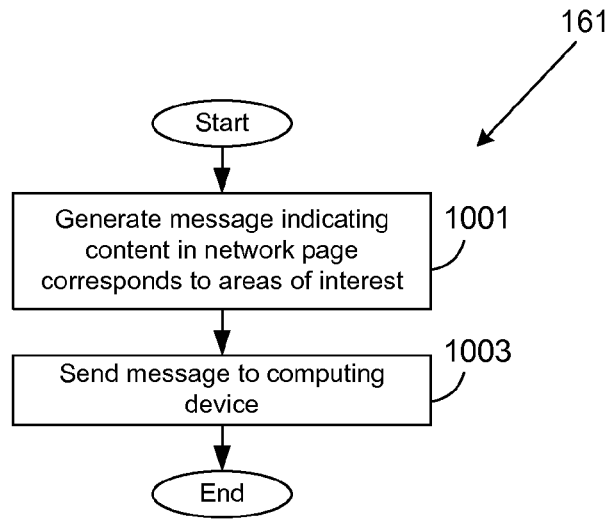
FIG. 10 is a flowchart illustrating an example of functionality of a position density map application implemented in a computing device in the networked environment of FIG. 1 according to various embodiments of the present disclosure.

Referring next to FIG. 10, shown is a flowchart that provides one example of the operation of a portion of the position density map application 161 according to various embodiments. It is understood that the flowchart of FIG. 10 provides merely an example of the many different types of functional arrangements that may be employed to implement the operation of the portion of the position density map application 161 as described herein. As an alternative, the flowchart of FIG. 10 may be viewed as depicting an example of steps of a method implemented in the computing device 103 (FIG. 1) according to one or more embodiments.

In box 1001, the position density map application 161 generates a message indicating the content of the network page 121 that corresponds to the areas of interest 167. In box 1003, the position density map application 161 sends the message to an operator at an appropriate email address, etc. The operator can then take appropriate action to alter the network page in view of the areas of interest 167.

Figure 11:
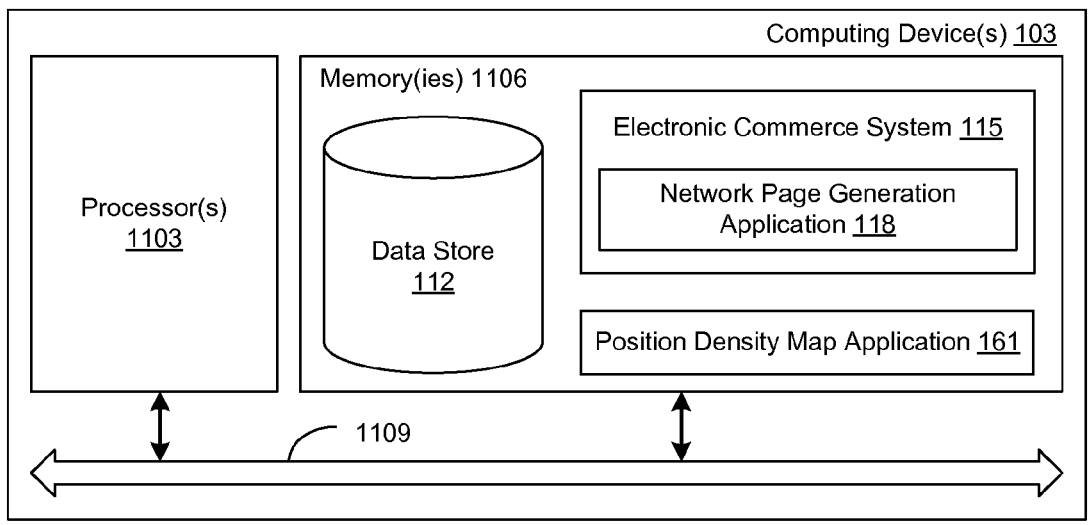
FIG. 11 is a schematic block diagram that provides one example illustration of a computing device employed in the networked environment of FIG. 1 according to various embodiments of the present disclosure.

With reference to FIG. 11, shown is a schematic block diagram of the computing device 103 according to an embodiment of the present disclosure. The computing device 103 includes at least one processor circuit, for example, having a processor 1103 and a memory 1106, both of which are coupled to a local interface 1109. To this end, the computing device 103 may comprise, for example, at least one server computer or like device. The local interface 1109 may comprise, for example, a data bus with an accompanying address/control bus or other bus structure as can be appreciated.

Stored in the memory 1106 are both data and several components that are executable by the processor 1103. In particular, stored in the memory 1106 and executable by the processor 1103 are the network page generation application 118, the position density map application 161, and potentially other applications. Also stored in the memory 1106 may be a data store 112 and other data. In addition, an operating system may be stored in the memory 1106 and executable by the processor 1103.

It is understood that there may be other applications that are stored in the memory 1106 and are executable by the processors 1103 as can be appreciated. Where any component discussed herein is implemented in the form of software, any one of a number of programming languages may be employed such as, for example, C, C++, C#, Objective C, Java, Java Script, Perl, PHP, Visual Basic, Python, Ruby, Delphi, Flash, or other programming languages.

A number of software components are stored in the memory 1106 and are executable by the processor 1103. In this respect, the term "executable" means a program file that is in a form that can ultimately be run by the processor 1103. Examples of executable programs may be, for example, a compiled program that can be translated into machine code in a format that can be loaded into a random access portion of the memory 1106 and run by the processor 1103, source code that may be expressed in proper format such as object code that is capable of being loaded into a random access portion of the memory 1106 and executed by the processor 1103, or source code that may be interpreted by another executable program to generate instructions in a random access portion of the memory 1106 to be executed by the processor 1103, etc. An executable program may be stored in any portion or component of the memory 1106 including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The memory 1106 is defined herein as including both volatile and nonvolatile memory and data storage components. Volatile components are those that do not retain data values upon loss of power. Nonvolatile components are those that retain data upon a loss of power. Thus, the memory 1106 may comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may comprise, for example, static random access memory (SRAM), dynamic random access memory (DRAM), or magnetic random access memory (MRAM) and other such devices. The ROM may comprise, for example, a programmable read-only memory (PROM), an erasable programmable read-only memory (EPROM), an electrically erasable programmable read-only memory (EEPROM), or other like memory device.

Also, the processor 1103 may represent multiple processors 1103 and the memory 1106 may represent multiple memories 1106 that operate in parallel processing circuits, respectively. In such a case, the local interface 1109 may be an appropriate network 109 (FIG. 1) that facilitates communication between any two of the multiple processors 1103, between any processor 1103 and any of the memories 1106, or between any two of the memories 1106, etc. The local interface 1109 may comprise additional systems designed to coordinate this communication, including, for example, performing load balancing. The processor 1103 may be of electrical or of some other available construction.

Although the network page generation application 118 and the position density map application 161, and other various systems or applications described herein may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits having appropriate logic gates, or other components, etc. Such technologies are generally well known by those skilled in the art and, consequently, are not described in detail herein.

The flowcharts of FIGS. 6-10 that shows the functionality and operation of an implementation of portions of the electronic commerce system 115, the network page generation application 118 and the position density map application 161. If embodied in software, each block may represent a module, segment, or portion of code that comprises program instructions to implement the specified logical function(s). The program instructions may be embodied in the form of source code that comprises human-readable statements written in a programming language or machine code that comprises numerical instructions recognizable by a suitable execution system such as a processor 1103 in a computer system or other system. The machine code may be converted from the source code, etc. If embodied in hardware, each block may represent a circuit or a number of interconnected circuits to implement the specified logical function(s).

Although the flowcharts of FIGS. 6-10 show a specific order of execution, it is understood that the order of execution may differ from that which is depicted. For example, the order of execution of two or more blocks may be scrambled relative to the order shown. Also, two or more blocks shown in succession in FIGS. 6-10 may be executed concurrently or with partial concurrence. Further, in some embodiments, one or more of the blocks shown in FIGS. 6-10 may be skipped or omitted. In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present disclosure.

Also, any logic or application described herein, including the network page generation application 118 and/or the position density map application 161, that comprises software or code can be embodied in any non-transitory computer-readable medium for use by or in connection with an instruction execution system such as, for example, a processor 1103 in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system. The computer-readable medium can comprise any one of many physical media such as, for example, electronic, magnetic, optical, electromagnetic, infrared, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

Therefore, the following is claimed:

1. A non-transitory computer-readable medium embodying a program executable in a computing device, wherein the program, when executed, causes the computing device to:
   receive a network page request from a client;
   generate a network page comprising content, the network page being generated based at least in part on the network page request;
   store implicit behavior data from the client associated with an instance of the network page from the client configured to access an electronic commerce system, the implicit behavior data relating to a user's interaction with the instance of the network page;
   generate a position density map from the implicit behavior data;
   determine that the position density map indicates that the implicit behavior data exceeds a first predefined threshold associated with a first region of the network page, wherein the first predefined threshold is based at least in part on a first content category associated with the first region of the network page and the first region of the network page being above a network page fold of the network page;
   determine that the position density map indicates that the implicit behavior data exceeds a second predefined threshold associated with a second region of the network page, wherein the second predefined threshold is based at least in part on a second content category associated with the second region of the network page;
   determine at least one area of interest associated with the network page based at least in part on the implicit behavior data exceeding the first predefined threshold or the second predefined threshold;
   store the position density map in a data store;
   generate an additional network page based at least in part on the at least one area of interest;
   run an A/B test associated with the additional network page; and
   store a plurality of results of the A/B test in the data store.

2. The non-transitory computer-readable medium of claim 1, wherein the plurality of results of the A/B test are selected from at least one of a plurality of requests for additional information, a plurality of referrals, a plurality of purchases, a plurality of click-throughs, a plurality of ratings, a plurality of requests for additional network pages, or a plurality of requests for an objective network page.

3. The non-transitory computer-readable medium of claim 1, wherein the content of the network page is selected from at least one of advertising content, service-based content, informational content, or entertainment content.

4. A method, comprising:
   generating, in at least one computing device, a plurality of instances of a network page to be rendered on a corresponding plurality of clients;
   storing, in the at least one computing device, implicit behavior data from the corresponding plurality of clients, the implicit behavior data relating to a user interaction with the plurality of instances of the network page, respectively;
   generating, in the at least one computing device, a position density map from the implicit behavior data;
   determining, in the at least one computing device, at least one region of interest associated with the network page based at least in part on the position density map indicating the implicit behavior data exceeding a respective one of a plurality of thresholds associated with the network page, the respective one of the plurality of thresholds being determined based at least in part on a content category associated with a portion of the network page and whether the portion of the network page is above a network page fold of the network page;
   correlating, in the at least one computing device, the at least one region of interest to a content of the network page; and
   implementing, in the at least one computing device, an action based at least in part on the implicit behavior data.

5. The method of claim 4, wherein the implicit behavior data further comprises a plurality of cursor positions within the network page.

6. The method of claim 4, wherein the implicit behavior data further comprises a plurality of highlighting positions within the network page.

7. The method of claim 4, wherein the implicit behavior data further comprises a time spent at a cursor position within the network page.

8. The method of claim 4, wherein the implicit behavior data further comprises a time spent at a scrolling position within the network page.

9. The method of claim 4, wherein the implicit behavior data further comprises a time spent highlighting an amount of text within the network page.

10. The method of claim 4, wherein the at least one region of interest is associated with the content of the network page with a level of user interaction above the respective one of the plurality of thresholds, and a plurality of remaining regions comprise the content of the network page with a level of user interaction below a second respective one of the plurality of thresholds.

11. The method of claim 4, wherein the action comprises changing, in the at least one computing device, the content of the network page.

12. The method of claim 4, wherein the action comprises:
generating, in the at least one computing device, a revised network page by moving the content associated with the at least one region of interest to a higher user visibility location relative to a prior position of the content;
moving, in the at least one computing device, remaining content to a lower visibility location relative to a prior position of the remaining content; and
storing, in the at least one computing device, the revised network page.

13. The method of claim 4, wherein the action comprises:
running, in the at least one computing device, an A/B test to identify an effect of revising the network page using the at least one region of interest; and
storing, in the at least one computing device, the effect of revising the network page as a plurality of results of the A/B test, the plurality of results comprising at least one of a plurality of click-throughs, a plurality of purchased items, or requesting an objective page.

14. The method of claim 4, wherein the action further comprises:
generating, in the at least one computing device, a message indicating that the content in the network page corresponds to the at least one region of interest; and
sending, in the at least one computing device, the message to a client device.

15. The method of claim 4, further comprising using, in the at least one computing device, other relevant data beyond the implicit behavior data in determining the at least one region of interest associated with the network page.

16. The method of claim 4, wherein the implicit behavior data is recorded at a plurality of discrete points in time.

17. A system, comprising:
at least one computing device; and
an application executable in the at least one computing device, wherein the application, when executed, causes the at least one computing device to:
generate a position density map associated with implicit behavior data, the implicit behavior data relating to an interaction of a plurality of users with a network page;
determine at least one region of interest associated with the network page based at least in part on the position density map indicating the implicit behavior data exceeding a respective one of a plurality of thresholds associated with the network page, the respective one of the plurality of thresholds being determined based at least in part on a content category associated with a portion of the network page and whether the portion of the network page is above a network page fold of the network page;
correlate the at least one region of interest to a content of the network page;
change the content of the network page based at least in part on the at least the at least one region of interest; and
identify an effect of the change of the network page.

18. The system of claim 17, wherein the application further causes the at least one computing device to:
generate the network page in response to a request;
store an initial page content of the network page; and
store the implicit behavior data from a client device.

19. The system of claim 17, wherein identifying the effect of the change of the network page further causes the at least one computing device to:
run a plurality of A/B tests to identify the effect;
generate a plurality of results from the plurality of A/B tests; and
store the plurality of results from the plurality of A/B tests.

20. The system of claim 17, wherein the content category is at least one of advertising content, service-based content, informational content, or entertainment content.

* * * * *